United States Patent [19]

Ritchey et al.

[11] 4,425,325
[45] * Jan. 10, 1984

[54] ORAL COMPOSITIONS

[75] Inventors: Thomas W. Ritchey, Norwood; John M. Weaver, North Bergen; Martin Sapone, Tenafly, all of N.J.

[73] Assignee: Lever Brothers Company, New York, N.Y.

[*] Notice: The portion of the term of this patent subsequent to Jul. 13, 1999 has been disclaimed.

[21] Appl. No.: 345,453

[22] Filed: Feb. 3, 1982

Related U.S. Application Data

[63] Continuation-in-part of Ser. No. 235,247, Feb. 17, 1981, Pat. No. 4,339,432, which is a continuation-in-part of Ser. No. 50,392, Jun. 20, 1979, and Ser. No. 50,393, Jun. 20, 1979.

[51] Int. Cl.³ .............................. A61K 7/16; A61K 7/22
[52] U.S. Cl. ........................................... 424/54; 424/49
[58] Field of Search ..................................... 424/49–58

[56] References Cited

U.S. PATENT DOCUMENTS

| | | | |
|---|---|---|---|
| 1,767,667 | 6/1930 | Gray | 424/145 X |
| 2,527,686 | 10/1950 | Sandberg | 167/93 |
| 3,095,396 | 6/1963 | Mantz | 260/29.4 |
| 3,622,662 | 11/1971 | Roberts et al. | 424/54 |
| 3,655,868 | 4/1972 | Vagebas | 424/54 |
| 3,772,431 | 11/1973 | Mlkvy et al. | 424/44 |
| 3,888,976 | 6/1975 | Mlkvy et al. | 424/44 |
| 4,020,158 | 4/1977 | Ashmead et al. | 424/289 X |
| 4,022,880 | 5/1977 | Vinson | 424/49 |
| 4,082,841 | 4/1978 | Pader | 424/50 |
| 4,100,269 | 7/1978 | Pader | 424/49 |
| 4,138,477 | 2/1979 | Gaffer | 424/52 |
| 4,144,323 | 3/1979 | Lamberti | 424/54 |
| 4,146,607 | 3/1979 | Ritchey | 424/54 |
| 4,152,418 | 5/1979 | Pader | 424/50 |
| 4,160,821 | 7/1979 | Sipos | 424/49 |
| 4,339,432 | 7/1982 | Ritchey et al. | 424/49 |

OTHER PUBLICATIONS

C.A. 68 #67077c #67078d(1968), 70 #94675u(1969), 73 #75863z(1970), 74 #115918a #117346g(1971), 80 #74331g #137182g(1974), 81 #6271h #41356m(1974), 82 #29947t(1975), 84 #29548e(1976), 87 #166391z(1977).

S. Wah Leung, "A Method for the In Vitro Production of Dental Calculus", J. Periodontology, 28 :217 (1956).

*Primary Examiner*—Shep K. Rose
*Attorney, Agent, or Firm*—James J. Farrell

[57] ABSTRACT

The astringency of an oral composition containing biologically active zinc ions may be reduced by the addition of glycine to the composition, and adjustment of the pH to about 4.5 to 9.4. In addition, zinc may be kept in a biologically active solution at this pH by the addition of glycine. The zinc-glycine combination serves as an anticalculus-antiplaque-antimalodor agent in oral compositions.

13 Claims, No Drawings

ORAL COMPOSITIONS

This application is a continuation-in-part application of Ser. No. 235,247 filed Feb. 17, 1981, now U.S. Pat. No. 4,339,432, which is a continuation-in-part application of Ser. No. 50,392 filed June 20, 1979 and Ser. No. 50,393 filed June 20, 1979.

BACKGROUND OF THE INVENTION

This invention relates to the field of oral products, particularly to toothpaste and mouthwash compositions.

It has been known to incorporate zinc salts into oral products for a variety of reasons. U.S. Pat. No. 2,527,686 discloses a mouthwash with zinc chloride, with no reason disclosed for its addition. U.S. Pat. No. 3,622,662 discloses zinc oxide and zinc phosphate as stabilizers in a dental cream. U.S. Pat. Nos. 3,772,431 and 3,888,976 disclose mouthwash tablets containing zinc salts as astringent-desensitizing agents. U.S. Pat. No. 3,095,396 discloses dentifrices with zinc salts added to inhibit the dissolving action of sodium metaphosphate.

The zinc ion has also been discovered to have anticalculus and antiplaque properties. The action of the zinc ion is discussed in U.S. Pat. No. 4,082,841, which relates to zinc salts in combination with enzymes. U.S. Pat. No. 4,022,880 discloses combinations of zinc salts with antibacterial agents, and U.S. Pat. No. 4,146,607 discloses zinc salts in combination with tetradecylamine. The antiplaque and anticalculus properties of zinc carboxymethyloxysuccinate are discussed in U.S. Pat. No. 4,144,323.

Despite the foregoing disclosures, the incorporation of zinc into oral products has posed some problems. The most soluble and highly ionized salts of zinc have the greatest bioactivity, zinc chloride being an example. However, due to the extremely small solubility product of zinc hydroxide ($1.2 \times 10^{-17}$), ionized zinc salts can only be kept in solution under acid conditions. Zinc chloride, for instance, must be kept at a pH less than 4.5. This presents some difficulty in formulation of a product with zinc salts, as it may be difficult to use desired ingredients that would raise the pH. Low pH also presents some problems with respect to the sour taste.

Certain zinc salts, such as the phenolsulfonate disclosed in U.S. Pat. No. 4,022,880, and the carboxymethyloxysuccinate disclosed in U.S. Pat. No. 4,144,323 are less sensitive to pH change, and may be formulated in compositions having a pH range of 5 to 6.5. It has been discovered, however, that due to a slight interaction between the phenolsulfonate and cationic germicides, for instance, cetyl pyridinium chloride, the latter being a germicide also disclosed in U.S. Pat. No. 4,022,880, there is reduced germicidal activity.

Another problem of formulating an oral product with zinc salts is astringency, an organoleptically displeasing effect of the zinc ion. While certain of the aforementioned U.S. patents use zinc for its astringent properties, the astringency is not always desirable, and can be objectionable when the zinc salt is used at higher levels for more effective calculus control. U.S. Pat. No. 4,082,841 recommends using insoluble zinc salts to reduce astringency, while U.S. Pat. No. 4,144,323 discloses zinc carboxymethyloxysuccinate as a less astringent, but soluble zinc compound.

It has been discovered that the foregoing problems have been overcome by the instant invention, which is an oral composition containing zinc kept in solution at pH of about 4.5-9 using glycine. It has also been found that the compositions of the invention provide an antimalodor effect. Applicants have discovered that when glycine is added to certain solutions containing biologically active zinc, the pH may be raised as high as about 9.4 without precipitation of zinc hydroxide. There is also no interaction with many germicides. The astringency of mouthwashes may be substantially reduced at near neutral pHs and also by raising the pH of the zinc-glycine combinations, the astringency of the zinc is greatly reduced. Further, when glycine is added to certain solutions of biologically active zinc, the pH may be raised as high as 9.4 without precipitation of zinc compounds such as, for example, zinc hydroxide.

The use of glycine in an oral product is described in U.S. Pat. No. 3,655,868. This patent discloses the addition of glycine to copper gluconate in order to prevent the absorption of the gluconate by mucin in the mouth. The combination is also soluble at near neutral pHs, whereas the previously used copper gluconate-amino benzoate combination is not. The patent discloses that its usefulness lies in the presence of complexes of both gluconate and glycine. The instant invention requires no particular anion.

Applicants have discovered that zinc may be kept in a biologically active solution at a pH of about 4.5 to about 9.4 by the addition of glycine and that the astringency of an oral composition containing biologically active zinc may be reduced by the addition of glycine to the composition and by adjusting the pH to a range of about 4.5 to about 9.4. In this pH range, the solution, containing the biologically active zinc, is far less astringent than at a pH of below about 4.5. At a pH above about 9.4, the solubility of the zinc is greatly reduced and precipitation of zinc compounds such as, for example, zinc hydroxide is likely. Accordingly, an oral composition is provided having a pH of about 4.5 to about 9.4, comprising a physiologically acceptable zinc salt or compound and glycine. In certain instances, the salt zinc glycinate can be used directly as well as being formed in situ.

Glycine, also known as aminoacetic acid, is an amino acid of the formula:

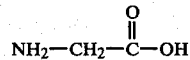

Glycine has been used as a nutrient and is non-toxic. It is also an excellent buffer and a natural sweetening agent. The concentration of glycine in the invention will vary from at least about 0.01% to about 7%, preferably from 0.1% to 3.0% by weight, depending on zinc concentration and desired pH, although there are no reasons why glycine cannot be used at higher levels since it is a non-toxic sweetening agent. The ratio of glycine to zinc most preferred is one part of zinc to two or more parts glycine.

Zinc from compounds, according to the present invention, will generally be present in the oral composition in an amount of from about 0.04% to about 2.0%. In the case of mouthwash products, the zinc salt or compound may be added at a level sufficient to produce about 0.04% to about 0.7% by weight of soluble zinc moieties, with 0.04% being the approximate minimum active concentration and 0.7% being the approximate concentration at which astringency becomes objectionable. In a dentifrice, the maximum concentration of zinc is about 30,000 ppm. Higher amounts can be used but it is not believed to be economical. The minimum is about 100 ppm. 6000 ppm is the optimum level. The solubility of the zinc glycine combination at levels above about 4000 ppm of zinc is enhanced if the pH of the dentifrice is adjusted to above about 7 for products containing up to about 20% by weight of water. At higher levels of water the zinc glycine combination can be present at higher levels and remain soluble.

In a rinse, the maximum concentration of zinc is about 8,000 ppm and the minimum about 50 ppm with 2,000 ppm being preferred. Since there is more water in a rinse than in a dentrifice, the zinc can be soluble and of acceptable astringency even at 8,000 ppm.

The addition of glycine to a zinc containing product or the use of zinc glycinate together with raising the pH permits the amount of zinc to be increased without producing objectionable astringency.

In addition to zinc glycinate, many pharmaceutically acceptable zinc salt or compound may be used. Included among these are acetate, benzoate, borate, bromide, carbonate, citrate, chloride, glycerophosphate, hexafluorosilicate, dl-lactate (trihydrate), nitrate, phenolsulfonate, silicate, alkanoates having 8–18 carbon atoms, salicylate, stannate, sulfate, tannate, tartrate, titanate, tetrafluoroborate, oxide, peroxide and hydroxide. The zinc compounds or salts may be used singly or in admixture.

The zinc salts or compounds may be added to the mouthwash or product as zinc glycinate directly, although the zinc salt and the glycine are usually added separately for convenience. The term "pharmaceutically acceptable" as used herein with reference to zinc compounds is applicable to those compounds which, under the conditions of use and in the compositions set forth herein, are safe and organoleptically tolerable in the oral cavity, and have no significant side effects either orally or systemically.

The balance of the oral composition in accordance with the present invention will consist of the usual carrier medium and other desired substances consistent with the form of the composition. For example, where the oral composition contemplated is a mouthwash, the balance of the preparation will usually contain water, or water and a mono- or polyhydric alcohol such as ethanol, glycerol, or sorbitol, and optionally, flavoring substances and foaming agents. Glycerol and sorbitol are also useful as an aid in sweetening the product. Surfactants and/or suspending agents are usually present in mouthwashes as solubilizers for essential flavoring oils. The customary solubilizers for this purpose are the sorbitan fatty acid esters, the polyoxyethylene derivatives thereof, and polyoxyethylene fatty acid ethers. In addition, the mouthwash formulation may contain one or more of the well known, highly active antibacterial agents, such as bis-biguanides, aliphatic amines, hexachlorophene, the salicylanilides, compatible quaternary ammonium compounds, and the like.

When the oral composition is in the form of a dentifrice or toothpaste, there may be present polishing agents, humectants, bodying agents, flavoring substances, sweetening substances, foaming agents, etc. It will be understood that the polishing agents and other components suitable for use in the toothpastes of the invention must be compatible with the zinc compounds.

Among the suitable inorganic polishing agents useful in accordance with the invention are the silica xerogels and silica aerogels manufactured by the Davison Chemical Division of W. R. Grace and Company, for example those available under the trade names of Syloid 63 and Syloid 65 (xerogels), and Syloid 244 (aerogel). The xerogels are synthetic, aggregated, amorphous, highly porous silicas having generally a mean particle diameter of about 4 to about 10 microns. The aerogel Syloid 244 has a mean particle diameter of about 3 microns and is more porous than the xerogels. Also useful are other polishing agents disclosed hereinafter as well as aluminas, precipitated silicas and the like.

The polishing agent should be in the form of fine particles, as is well known in the art. Preferably, the particles should be of such size that at least 40% pass through a 325 mesh screen, and at least 90% pass through a 20 mesh screen. The finer particles within this size range are preferred, particularly a size distribution such that all the particles pass through a 20 mesh screen; more than 90% pass through a 100 mesh screen; more than 80% pass through a 200 mesh screen; and more than 40% pass through a 325 mesh screen. Especially preferred are the finer particles having a mean particle diameter of about 3 to about 44 microns.

Polymer particles of various types are useful as abrasives. A particularly useful polymer is polyethylene in powder form of such size that more than 40% passes through a 325 mesh screen; more than 80% passes through a 200 mesh screen; at least 85% passes through a 100 mesh screen; and 90 to 100% passes through a 20 mesh screen. Such polyethylene polymers are sold under the trade names Super Dylan Polyethylene J-1 or J-2 powder, available from ARCO/Polymers, Inc.

Other substances proposed as dental abrasives include various abrasive materials such as silica embedded in protective plastic particles, chalks, metaphosphates, abrasives, and dicalcium phosphate dihydrate.

Polishing agents will be present in the toothpaste of the invention over the broad range of about 1% to 70%, preferably 10% to 60%, and typically from about 20% to 50%. In a tooth powder the polishing agent will be present over the range of about 50% to 99%, preferably from about 70% to 95%, and typically from about 90% to about 95%.

The toothpastes will usually contain compatible bodying agents such as gum Karaya, gum Tragacanth, starch, sodium carboxymethylcellulose, Irish moss, gum arabic, sodium carboxymethylhydroxyethylcellulose, polyvinylpyrrolidone, etc. When present, these will usually be at levels of from about 0.5% to about 3%, preferably from about 0.8% to about 1.5%.

Humectants are desirable in a toothpaste to provide smooth texture and flowability. These will usually be such compounds as glucose, honey, glycerol, propylene glycol, hydrolyzed hydrogenated starch, sorbitol, polyethylene glycol 400, and other polyhydric alcohols, and may be present in the composition in amounts of up to about 80% by weight.

Other adjuvants may be present, such as fluorides, chlorophyll compounds, flavoring substances, saccharin, urea, ammonium compounds, alcohol, mineral oil, and foaming agents or detergents, such as sodium lauryl sulfate, dodecanesulfonate, acyl taurines, acyl isethionates, etc., depending upon the form of the product.

The various chemical compounds present in the oral compositions may themselves result in attainment of the desired pH of about 4.5 to about 9.4. If the pH of the formulation remains below 4.5, any alkaline material suitable for use in an oral composition and compatible with the other ingredients may be used to adjust the pH. Sodium hydroxide, sodium carbonate and sodium bicarbonate are typical. If the pH is above about 9.4, where precipitation of zinc compounds such as hydroxide is likely, any acid buffer, suitable for use in an oral composition and compatible with the other ingredients, may be added for example hydrochloric acid.

Oral products containing the zinc-glycine mixture may, in addition, contain other ingredients identified as acting synergistically with the zinc to prevent calculus, plaque and malodor, such as the antibacterial agents of U.S. Pat. No. 4,022,880 and the enzymes of U.S. Pat. No. 4,082,841.

The invention is illustrated by the following examples. All percentages herein are by weight.

EXAMPLE 1

Solubility Testing

To aqueous solution of zinc chloride at levels of 0.172% (0.0126 M) and 0.344% (0.0252 M), were added glycine at levels of 0.1% (0.0132 M), 0.2% (0.0266 M), 0.4% (0.0432 M), and 0.8% (0.106 M). The pH of each solution was raised from 4 to 8 with NaOH, and the point at which $Zn(OH)_2$ precipitated was noted. The results are given in Table 1 below.

TABLE 1

| $ZnCl_2 \downarrow$ | 0 | (.0132M) .1% | (.0266M) .2% | (.0532M) .4% | (.106M) .8% | glycine |
|---|---|---|---|---|---|---|
| 0.172% (.0126M) | p = 4.8 | p = 7-8 | p = 7-8 | * | * | |
| 0.344% | p = 4.8 | p = 6.5 | p = 6.5 | p = 6.5 | p = 6.5 | | p = pH of precipitation.
* = stable at pH 8.

EXAMPLE 2

Solutions were prepared with 0.172% $ZnCl_2$ and glycine at levels of 0.1%, 0.2%, 0.4%, 0.8% at pHs of 4.8, 5.5 and 6.5. All solutions remained stable over a six-week period with no precipitation.

EXAMPLE 3

An in vitro dipping test was used to determine whether the zinc ion with glycine was an effective anticalculus agent. The basic test is described in an article by S. Wah Leung, "A New Method for the In Vitro Production of Dental Calculus", *J. Periodontology,* 28:217 (1956), and is modified as described herein.

The creation of dental calculus was simulated on frosted glass plummets by continuously dipping them in a calcifying solution. Each dipping cycle consisted of a 30 second immersion in the solution followed by 30 seconds air drying. The dipping apparatus was enclosed in a constant temperature cabinet at 36°±1° C. at high humidity.

Daily anticalculus treatment consisted of 5 minutes dipping in distilled water, 1 minute immersion in a test solution and another 5 minute dipping in distilled water. Dipping in a calcifying solution as describe above is then repeated.

The calcifying solution is made with porcine glycoprotein, which has similar properties to human mucin. The submaxillary gland of a pig is minced, extracted three times with water in a Waring Blender for five minutes each, stirred at low speed for 18 hours, centrifuged in 250 ml bottles at least 15,000 G for 30 minutes, and lyophilized in a Stoken Freezer Dryer for two days. All procedures were carried out at 4° C. The mucin is desiccated in 5 gm quantities at 40° C.

A new calcifying solution is prepared each day by adding the lyophilized mucin to 135 ml $CaCO_3$ solution and 15 ml $PO_4$ buffer, then bubbling with $CO_2$ until the mucin is dissolved. The $CaCO_3$ solution is prepared by adding 0.070 grams of $CaCO_3$ to 540 ml water, and bubbling with $CO_2$ until the carbonate dissolves. The phosphate buffer (pH=7) is a mixture of 8 grams $NaH_2PO_4$ and 9.47 grams $Na_2HPO_4$ in one liter of water.

After 8 days of dipping, the plummets are desiccated for 24 hours at 40° C., and analyzed for calcium and phosphorous. The Ca/P ratio is determined and compared with the ratios for actual dental calculus, which vary from 1.28 to 1.55.

The results of the dipping test are shown in Table 2. For comparison, results for zinc carboxymethyloxysuccinate [$Zn_3(CMOS)_2$], which may be formulated at a higher pH than zinc chloride, are also given.

TABLE 2

| | conc. | pH | Ca/P |
|---|---|---|---|
| $H_2O$ | 100% | 5.3 | 1.25 |
| CPC | .04% | 5.3 | 1.30 |
| $ZnPS.8 H_2O$ | .67 | 5.3 | 0.83 |
| $ZnCl_2$ | .172% | 4.3 | 0.81 |
| $ZnCl_2$ + glycine | .172% .5% | 5.3 | 0.85 |
| $ZnCl_2$ + glycine + CPC | .172% .5% .04% | 5.3 | 0.85 |
| $Zn_3(CMOS)_2$ | .2% | 5.3 | 1.13 |

ZnPS = zinc phenolsulfonate
CPC = cetyl pyridinium chloride

EXAMPLE 4

Astringency Testing

Four mouthrinses were prepared with the following compositions:

| RINSE A | Zinc chloride | 0.172% |
|---|---|---|
| | HCl | to pH 4.3 |
| | Water | Balance to 100% |
| RINSE B | Zinc chloride | 0.172% |
| | Glycine | 0.500% |
| | NaOH | to pH 4.3 |
| | Water | Balance to 100% |
| RINSE C | Zinc chloride | 0.172% |
| | Glycine | 0.500% |
| | NaOH | to pH 7.2 |
| | Water | Balance to 100% |
| RINSE D | Zinc chloride | 0.172% |
| | Glycine | 0.500% |
| | $Na_2CO_3$ | to pH 7.2 |
| | Water | Balance to 100% |

Ten subjects compared these rinses on three consecutive days. A and B were compared on day 1, B and C on day 2, and C and D on day 3. All subjects rinsed with 20 ml of each rinse for 30 seconds. The two rinses were sampled by each subject four hours apart.

No significant differences were found in astringency between Rinses A and B, or C and D. However, Rinses B and C showed a significant difference from each other, Rinse C being much less astringent.

Both Rinses B and C contained zinc and glycine, the difference between the two being the pH. The presence of glycine enabled the pH to be raised to a point where the zinc was less astringent. No improvement was noted by the substitution of sodium carbonate for sodium hydroxide as the buffer.

Examples 5 and 6 set forth a mouthwash according to the invention herein.

EXAMPLE 5

Mouthwash

| Ingredient | % Weight |
| --- | --- |
| Ethanol | 22.00% |
| Glycerol | 12.00 |
| Flavor, color | .90 |
| Zinc chloride | .25 |
| Glycine | .80 |
| Cetyl pyridinium chloride | .05 |
| Polyoxyethylene (20) Sorbitan monolaurate* | .20 |
| NaOH | to pH 6.5 |
| Water | Balance to 100% |

*Marketed by Hodag Chemical Company as Polysorbate 20, and Atlas Chemical Company as Tween 20.

EXAMPLE 6

Mouthwash

| Ingredient | % Weight |
| --- | --- |
| Glycerol | 8.00% |
| Flavor | .15 |
| Saccharin | .02 |
| FD&C Yellow No. 6 (.7% solution) | .10 |
| FD&C Red No. 2 (.2% solution) | .12 |
| Zinc sulfate | .40 |
| Glycine | 1.80 |
| Sodium lauryl sulfate | .33 |
| Polyoxyethylene (20) Sorbitan monolaurate* | .30 |
| NaOH | to pH 7.2 |
| Water | Balance to 100% |

Examples 7 and 8 set forth a toothpaste or dentifrice according to the invention herein.

EXAMPLE 7

Toothpaste

| Ingredient | % Weight |
| --- | --- |
| Silica Xerogel (Syloid 63) | 10.00 |
| Humectant (Sorbitol) | 40.00 |
| Sodium Lauryl sulfate (21% in glycerine) | 7.00 |
| Bodying Agent (Na Carboxymethylcellulose) | 1.00 |
| Flavor, color | 1.50 |
| Zinc chloride | 1.00 |
| Glycine | 2.00 |
| NaHCO3 | to pH 6.0 |
| Water | Balance to 100% |

EXAMPLE 8

| Ingredient | % Weight |
| --- | --- |
| Silica Xerogel (Syloid 63) | 15.00 |
| Powdered Polyethylene | 5.00 |
| Na Carboxymethylcellulose | .80 |
| Glycerol | 65.00 |
| Saccharin | .20 |
| Zinc chloride | .60 |
| Glycine | 1.50 |
| Flavor | 1.30 |
| Coloring Agent | .25 |
| Foaming Agent | .65 |
| NaOH | to pH 6.3 |

| Ingredient | % Weight |
| --- | --- |
| Water | Balance to 100% |

*High density polyethylene powder, average particle size 8-9 microns.

EXAMPLE 9

Toothpaste

| Ingredient | % Weight |
| --- | --- |
| Syloid 63X | 14.00 |
| Syloid 244 | 11.00 |
| Xanthan Gum | 0.4 |
| Zinc Glycinate | 10.00 |
| Sodium Benzoate | 0.08 |
| Polyethylene glycol | 5.00 |
| Hydrolyzed Hydrogenated Starch | 33.5 |
| Sodium Saccharin | 0.45 |
| Sodium lauryl sulfate | 1.6 |
| Flavor and colorants | 3.16 |
| Alcohol | 2.1 |
| Sodium hydroxide | to pH 8.5 |
| Water | Balance to 100% |

The invention has been described with respect to certain preferred embodiments. Various modifications and variations in lieu thereof will be suggested to persons skilled in the art, and are to be included within the spirit and purview of this application and within the scope of the appended claims.

What is claimed is:

1. An oral composition having a pH of about 4.5 to about 9.4 comprising a physiologically acceptable zinc compound at a level sufficient to produce about 50 to about 30,000 parts per million of zinc wherein said zinc compounds may have a tendency to produce the organoleptically displeasing effect of astringency and glycine at a level of about 0.01% to about 7% by weight, based on the total weight of the composition as the essential effective agent reducing astringency or said glycine serving to effectively solubilize said zinc compounds.

2. The composition according to claim 1 wherein the zinc salt is zinc chloride.

3. The composition according to claim 1 wherein the zinc compound is zinc glycinate.

4. The composition according to claim 1 wherein the zinc compound is present at a level sufficient to produce about 6,000 ppm of zinc.

5. The composition according to claim 1 wherein the glycine is present at a level of about 0.1% to about 3% by weight.

6. The composition according to claim 1 wherein glycine is present in a ratio of at least about two parts glycine to one part zinc.

7. The composition according to claim 1 which is in the form of a mouthwash and wherein the zinc compound is present at a level sufficient to produce about 0.04% to about 0.7% by weight of soluble zinc.

8. A method for reducing the astringency of an oral composition containing biologically active zinc in an amount of about 50 to about 30,000 parts per million comprising adding glycine to said composition in an amount of from at least about 0.01% to about 7% by weight and adjusting the pH of said composition to about 4.5 to about 9.4.

9. The method defined in claim 8 wherein the oral product is a mouthwash.

10. The method defined in claim 8 wherein the oral product is a toothpaste.

11. The method defined in claim 8 wherein the zinc is supplied by zinc chloride.

12. The method defined in claim 8 wherein the pH is adjusted to about 7.

13. The method of claim 8 wherein the glycine is present in a ratio of at least about 2 parts glycine to 1 part zinc.

* * * * *